United States Patent
Xu et al.

(10) Patent No.: US 11,248,002 B2
(45) Date of Patent: Feb. 15, 2022

(54) SESQUITERPENE DERIVATIVE AND USE OF THE SAME IN PREPARATION OF MEDICAMENT FOR TREATING HEPATITIS B DISEASES

(71) Applicant: KUNMING UNIVERSITY OF SCIENCE AND TECHNOLOGY, Kunming (CN)

(72) Inventors: Min Xu, Kunming (CN); Haoyang Yuan, Kunming (CN); Haizhou Li, Kunming (CN); Yingjun Zhang, Kunming (CN); Chongren Yang, Kunming (CN)

(73) Assignee: KUNMING UNIVERSITY OF SCIENCE AND TECHNOLOGY, Kunming (CN)

( * ) Notice: Subject to any disclaimer, the term of this patent is extended or adjusted under 35 U.S.C. 154(b) by 0 days.

(21) Appl. No.: 16/976,463

(22) PCT Filed: Feb. 26, 2019

(86) PCT No.: PCT/CN2019/076134
§ 371 (c)(1),
(2) Date: Aug. 27, 2020

(87) PCT Pub. No.: WO2019/165953
PCT Pub. Date: Sep. 6, 2019

(65) Prior Publication Data
US 2021/0047341 A1 Feb. 18, 2021

(30) Foreign Application Priority Data
Feb. 27, 2018 (CN) .......................... 201810163985.8

(51) Int. Cl.
*C07D 493/10* (2006.01)
(52) U.S. Cl.
CPC ................ *C07D 493/10* (2013.01)

(58) Field of Classification Search
CPC .................................................. C07D 493/10
See application file for complete search history.

(56) References Cited

FOREIGN PATENT DOCUMENTS

| CN | 103880856 B | 1/2017 |
|---|---|---|
| CN | 108164545 A | 6/2018 |

OTHER PUBLICATIONS

Lv et al. in Organic and Biomolecular Chemistry, 12, 8764 (2014) (Year: 2014).*
International Search Report (PCT/CN2019/076134); dated May 30, 2019.
Namphung Vongvanich et al."Phyllanthusols A and B, Cytotoxic Norbisabolane Glycosides from Phyllanthus Acidus Skeels"Mar. 8, 2000.
D. G. Durham et al."Extraction of Phyllanthusols A and B from Phyllanthus Acidus and Analysis by Capillary Electrophoresis"Dec. 31, 2002.

* cited by examiner

*Primary Examiner* — Dennis Heyer
(74) *Attorney, Agent, or Firm* — W&G Law Group (57) ABSTRACT

Disclosed are a sesquiterpene derivative and a use of the same in preparation of a medicament for treating hepatitis B diseases. The sesquiterpene derivative has the effects of down-regulating the hepatocyte nuclear factor 4α (HNF-4α) and significantly inhibiting the hepatitis B virus, and can be used for preventing and/or treating and/or assisting in the treatment of liver system diseases and symptoms caused by the hepatitis B virus, and can be used as a hepatic protective agent. In addition, the synthetic sesquiterpene derivative can also be used for preventing or treating viral infectious diseases and conditions resulting from the influenza virus, coxsackievirus, herpes simplex virus, etc. Also involved is the preparation of the synthetic sesquiterpene derivative, which acts as a raw material, in clinically acceptable pharmaceutical formulations, such as oral dosage forms such as tablets, capsules and drop pills or non-oral dosage forms such as inhalants and injections.

8 Claims, 4 Drawing Sheets

SESQUITERPENE DERIVATIVE AND USE OF THE SAME IN PREPARATION OF MEDICAMENT FOR TREATING HEPATITIS B DISEASES

FIELD

The present invention relates to the field of medical technology, and particularly, to a sesquiterpene derivative that is beneficial to the treatment of hepatitis B virus-infected hepatitis as well as liver damage system diseases and symptoms caused by virus infection.

BACKGROUND

Hepatitis B virus (HBV) may cause acute and chronic human hepatitis, which may induce cirrhosis or liver cancer, thereby affecting the lives of more than 2 billion people worldwide. The hepatitis B vaccine was successfully developed in 1982. Yet there are still more than 350 million HBV carriers in the world, and 500,000 to 1.5 million people die of hepatitis B virus infection each year, 50% of which are from the Asia-Pacific region. China has the largest population infected with hepatitis B virus, about 130 million HBV carriers, and about 300,000 people die of HBV infection every year. Nucleoside drugs acting on HBV DNA polymerase, although obviously resistant to hepatitis B virus, cannot completely eliminate the virus in patients, long-term application is prone to drug resistance. Therefore, anti-hepatitis B virus drugs have limited structural types, single target, and are highly toxic and prone to drug resistance in clinical applications. At the same time, there are also problems of low bioavailability and excessive metabolism.

Natural products, as prototypic or lead compounds, play an important role in the discovery of antiviral drugs. In the 1980s, it was first discovered that the extract of *Phyllanthus amarus* Schumach. & Thonn. has antiviral activity. Since then, Applicant has extracted and obtained the anti-hepatitis B virus main components from the *Phyllanthus acidus*, i.e., phyllanthacidoid ester derivatives, which showed good anti-HBV activity while significant toxicity was observed as well.

SUMMARY

In view of the deficiencies of the prior art, an object of the present invention is to provide a sesquiterpene derivative and a use thereof in the preparation of a medicament for treating hepatitis B diseases.

For the above objection of the present invention, the present invention provides a sesquiterpene derivative, which has a structure represented by the following structural formula I, II, III or IV:

wherein in the structural formula I and the structural formula II, $R_1$ is independently selected from the group consisting of benzoate group, p-hydroxybenzoate group, and hydrogen; in the structural formula III and the structural formula IV, $R_1$ is independently selected from n-hexylamino, n-heptylamino, n-octylamino, phenethylamino, iso-propoxypropylamino, ethoxypropylamino, n-hexyl ester group, n-heptyl ester group, n-octyl ester group, phenethyl ester group, iso-propoxypropyl ester group, and ethoxypropyl ester group.

Further, the sesquiterpene derivative preferably has a structure represented by the structural formula I, and $R_1$ is preferably the benzoate group or the p-hydroxybenzoate group.

The present invention further provides a use of the sesquiterpene derivative in preparation of a medicament for treating hepatitis B diseases.

Further, the hepatitis B diseases comprise hepatitis B virus-infected hepatitis, and liver damage diseases caused by hepatitis B virus infection.

Further, the sesquiterpene derivative is combinable with a pharmaceutically acceptable carrier and/or an edible carrier.

Further, the sesquiterpene derivative is contained in the medicament in a therapeutically effective dose.

Further, the therapeutically effective dose is sufficient to downregulate hepatocyte nuclear factor 4α.

Further, the medicament includes oral administration preparations and non-oral administration preparations. The oral administration preparations include tablets, pills, capsules, granules, microencapsulated tablets, suspensions, dropping pills, and oral liquids. The non-oral administration preparations include injections, aerosols, suppositories, and subcutaneous administration preparations.

The present invention has the following beneficial effects. The present invention relates to new medical uses of the sesquiterpene derivatives, i.e., pentyl esters or amides of phyllanthacidoid or any derivatives thereof that exhibit activities in hepatitis B virus infection diseases of laboratory animals. Specifically, it relates to that hepatocyte nuclear factor 4α (HNF-4α) is downregulated by pentyl esters or amides of phyllanthacidoid or any derivatives thereof, and synthetic or semi-synthetic compositions containing a mixture of pentyl esters or amides of phyllanthacidoid or any derivatives thereof, having significant inhibitory activity against hepatitis B virus. Compared with current medicaments for treating hepatitis B virus infection, the pentyl esters or amides of phyllanthacidoid or any derivatives thereof have enhanced/improved toxicological safety (i.e., reduced toxicity), enhanced/improved metabolic stability, and a longer half-life and/or slight side effects, while causing similar or increased biological activity (efficacy). They can be used to prevent or treat hepatitis B virus-infected diseases and conditions and function as a liver protectant for liver damages caused by hepatitis B virus, alcohol and liver damages caused by fatty liver. In addition, they can be used as a chemical tool medicament for the researches regarding hepatitis B infection or liver injury system disease mechanism related to hepatocyte nuclear factor 4α (HNF-4α) and virus biology.

Recently, Applicants have synthesized and applied the compounds represented by the structural formulas I, II, III and IV and intermediates thereof, of which the derivatives PA-XY1 and PA-XY2 can effectively inhibit surface e antigen and s antigen of the hepatitis B virus respectively with $IC_{50}$ (half maximal inhibitory concentration) values of 530 nM and 10 nM, which are much more effective than the positive controls Lamivudine and Besenol and show no cytotoxicity at a high concentration of 500 μM. Further study showed that its median effective dose in mice is 20 mg/kg, the maximum daily dose of mice is 2000 mg/kg with no toxic reactions observed in 7 days. The anti-hepatitis B virus efficiency showed linear increased pharmacological characteristics with increasing concentrations, indicating that the medicament is a highly effective and low-toxic anti-hepatitis B virus drug. Thus, it can be used to prepare medicaments for treating hepatitis B, chronic cirrhosis and other diseases.

DESCRIPTION OF EMBODIMENTS

Applicants found that the at least one symptom of pathological states of many liver system diseases such as hepatitis C, liver damage, liver cancer, etc., can be alleviated by down-regulating the hepatocyte nuclear factor 4α (HNF-4α). Therefore, individuals suffering from these diseases may be administrated with composition of pentyl esters or amides of phyllanthacidoid (or, as one main active component, one of analogues or congeners that are structurally similar to the pentyl esters or amides of phyllanthacidoid).

In addition, it is an important method to explore the pathogenesis of the liver system diseases such as hepatitis B, hepatitis C, liver damages and other virus infected diseases by studying the hepatocyte nuclear factor 4α (HNF-4α). The pentyl esters or amides of phyllanthacidoid involved in the present invention can significantly down-regulate the hepatocyte nuclear factor 4α (HNF-4α). Therefore, the pentyl esters or amides of phyllanthacidoid involved in the present invention (or, as one main active component, one of analogues or congeners that are structurally similar to the pentyl esters or amides of phyllanthacidoid) can be employed to study the pathogenesis of the liver or viral hepatitis system diseases.

Hepatitis B is a viral infectious disease caused by the hepatitis B virus. The disease has the characteristics of a long course of disease and repeated attacks, which may even cause cirrhosis, liver cancer, and eventually death. The hepatitis B is difficult to cure once suffering from it. Currently, no drugs that may functionally effectively inhibit the hepatitis B virus replication are available in clinical. The anti-hepatitis B medicament treatment will be endured for the whole life.

Nucleoside and interferons are known clinical medicaments. The interferons have significant side effects, which may lead to substantial impacts on health in a long-term use. The nucleosides have the problem of drug resistance. For example, lamivudine, the first-line drug for treating hepatitis B, may produce drug resistance and cannot completely eliminate cccDNA produced in the case of hepatitis B virus infection, and thus it cannot effectively cure the hepatitis B. In addition, traditional Chinese medicine products have the characteristics such as insignificant efficacy and unclear targets, and thus are less competitive in the market.

So far, no innovative anti-hepatitis B medicaments have been produced and come into the market in China. At present, the anti-hepatitis B drug market in China is dominated by imported drugs having relatively high price, which is less affordable for most patients, and may also cause economic problems in long-term use. Thus, they can hardly solve the problems of low medical treatment rate of hepatitis B in China. At the same time, the existing medicaments have relatively severe side effects or significant drug resistance, which can result in great impacts in the long-term use.

The present invention aims to treat the hepatitis B. In other words, the pentyl esters or amides of phyllanthacidoid composition and pharmaceutical formulations and compositions in the present invention exhibit significant "anti-hepatitis B virus activity", which is substantiated by the reduced viral replication and liver damage in hepatitis B-infected model animals. Therefore, the pentyl esters or amides of phyllanthacidoid composition and pharmaceutical formulations and compositions in the present invention can be used to the treatment of, not limited to, the following conditions: hepatitis B, liver damages.

The pentyl ester or amide of phyllanthacidoid according to the present invention has 8 chiral stereo centers. Therefore, the pentyl esters or amides of phyllanthacidoid can be used as a mixture of racemes (or diastereomers), a mixture of R and S enantiomers (or diastereomers) or pure enantiomers (R or S) (or diastereomers), which have been proved to have better biological activity. Eutomer is the pure enantiomer exhibiting better biological activity, and distomer is the enantiomer having lower biological activity.

The pentyl ester or amide of phyllanthacidoid according to the present invention has 3 free hydroxyl groups. Thus, the pentyl esters or amides of phyllanthacidoid can be used as salts and/or esters, which have been substantiated to have better biological activity and/or better metabolic parameters.

The effective pharmaceutical formulations and compositions of the present invention can be applied to treat the hepatitis B diseases and disorders as well as liver damage diseases and disorders. Although these pharmaceutical preparations are commonly used in the treatment of human patients, they can also be used to treat similar or identical diseases in animals such as primates, poultries such as chickens, ducks, or geese, farms animals such as pigs and cattle, and pets such as dogs and cats.

In the present invention, the pharmaceutically acceptable carriers include, but are not limited to, calcium carbonate, calcium phosphate, calcium sulfate, sucrose, glucose, lactose, fructose, xylitol, sorbitol, starch, starch paste, cellulose derivatives, gelatin, polyvinylpyrrolidone, sodium chloride, dextrin, stearic acid, magnesium stearate, calcium stearate, vegetable oil, polyethylene glycol, sterile phosphate buffered saline, saline, Ringer's solution, and combinations thereof.

In the present invention, the pharmaceutically acceptable salts include sodium salt, potassium salt, lithium salt, zinc salt, aluminum salt, calcium salt and magnesium salt.

The oral formulations of the present invention include, but are not limited to, solid oral administration formulations such as enteric coated tablets, dropping pills, oral tablets, chewable tablets, granules, powders or capsules; or liquid oral administration formulations such as syrup or tincture. In addition, the pentyl esters or amides of phyllanthacidoid and derivatives thereof or compositions thereof in the present invention can also be added to foods and beverages for oral administration. In addition, the pentyl esters or amides of phyllanthacidoid and the derivatives or compositions thereof in the present invention can also be formulated as chewing gum to facilitate oral delivery and absorption.

The non-oral administration formulations of the present invention include, but are not limited to, injection, or administrations in other systemic routes such as transdermal administration or transmucosal administration (for example, nasal administration, sublingual administration, buccal administration, administration via vagina or rectum, or administration through suppositories). Other routes of administration (for example, for veterinary applications) include enteral and parenteral deliveries, which include intramuscular, subcutaneous and/or intramedullary injections, as well as intrathecal injections, direct intraventricular injections, intravenous injections, intraperitoneal injections, intranasal injection or intraocular injection.

The pentyl esters or amides of phyllanthacidoid and the derivatives or compositions thereof involved in the present invention can be used in combination with other pharmaceutical active ingredients to prepare other new pharmaceutical compositions.

In the present invention, the pentyl esters or amides of phyllanthacidoid or derivatives thereof, or combinations thereof have verified efficacy and treatment-related activity to alleviate the above-mentioned symptoms, which were verified by assays and screening methods in the hepatitis B virus-infected mice.

In the present invention, the therapeutic effect, good metabolism parameters and common non-toxicity of the pentyl esters or amides of phyllanthacidoid or any derivatives thereof, or combinations thereof allow the compounds of the present invention to be used as ideal medicaments for treating the above-mentioned diseases.

The sesquiterpene derivatives of the present invention have the following structures:

-continued

III

-continued

IV

The preparation of the sesquiterpene derivative includes the following steps:

1. 10 g of rhizome of *Phyllanthus acidus* was extracted three times with refluxed methanol to obtain 429 g of extract. The crude extract was dispersed with 5.5 L of $H_2O$, and extracted 5 times with an equivalent volume of ethyl acetate and n-butanol. The n-butanol extraction layer was concentrated to dryness, dissolved in methanol, and separated with the macroporous resin column Diaion HP20SS chromatography eluting with $CH_3OH/H_2O$ (0-100)

(V/V %), to obtain 5 fractions. The fractions 2 and 3 were combined and separated with Sephadex LH20 (CH$_3$OH 0-100%) column chromatography to obtain other 5 fractions, of which the first two fractions (41.0 g) were combined and then repeatedly purified with a positive silica gel column chromatography (CHCl$_3$—CH$_3$OH—H$_2$O, 9:1:0-7:3:0.5), a negative silica gel column chromatography P-8 (CH$_3$OH 30%-80%) and gel resin column Toyopearl HW 40C (CH$_3$OH 0-30%) to prepare high-performance liquid chromatography (CH$_3$CN 15%-30%), to obtain phyllanthacidoid A (10 g) and phyllanthacidoid B (1 g).

2. Phyllanthacidoids A and B ($1.27*10^{-5}$ mol) were respectively dissolved in 1 ml of 0.72 M potassium carbonate aqueous solution and hydrolyzed at 60° C. for two hours to produce phyllanthacidoid aglycones A and B.

3. Phyllanthacidoid aglycone A was dissolved in an organic solvent, and reacted with 20-fold molar equivalents of n-amylamine for 12 hours to produce PA-XY1.

4. Phyllanthacidoid aglycone B was dissolved in an organic solvent, and reacted with 20-fold molar equivalents of n-amylamine for 12 hours to produce PA-XY2.

5. PA-XY1 or PA-XY2 was dissolved in 2M sodium hydroxide solution in which dioxane and water (1:1) were solvent, and hydrolyzed at 70° C. for 6 hours, separated and purified to obtain PA-XY3.

6. Phyllanthacidoid aglycone A was dissolved in an organic solvent, and reacted with 367-fold molar equivalents of n-pentanol at room temperature for 12 hours to produce PA-XY4.

7. Phyllanthacidoid aglycone A was dissolved in 1 ml of potassium carbonate solution, and reacted with 367-fold molar equivalents of n-pentanol at room temperature to produce PA-XY5.

8. PA was dissolved in 1 ml of 2M sodium hydroxide solution, hydrolyzed at 70° C. for 1 hour, and after removing the solvent, reacted with 1-fold molar equivalent of n-pentane bromide at room temperature to produce PA-XY6.

9. Phyllanthacidoid aglycone A was dissolved in an organic solvent, and reacted with 20-fold molar equivalents of n-hexylamine at room temperature for 12 hours to produce PA-XY7.

10. Phyllanthacidoid aglycone A was dissolved in an organic solvent, and reacted with 367-fold molar equivalents of n-hexanol at room temperature for 12 hours to produce PA-XY8.

11. Phyllanthacidoid aglycone A was dissolved in an organic solvent, and reacted with 20-fold molar equivalents of n-heptylamine at room temperature for 12 hours to produce PA-XY9.

12. Phyllanthacidoid aglycone A was dissolved in an organic solvent, and reacted with 367-fold molar equivalents of n-heptanol at room temperature for 12 hours to produce PA-XY10.

13. Phyllanthacidoid aglycone A was dissolved in an organic solvent, and reacted with 20-fold molar equivalents of n-octylamine at room temperature for 12 hours to produce YHY11.

14. Phyllanthacidoid aglycone A was dissolved in an organic solvent, and reacted with 367-fold molar equivalents of n-octanol at room temperature for 12 hours to produce PA-XY12.

15. Phyllanthacidoid aglycone A was dissolved in an organic solvent, and reacted with 20-fold molar equivalents of phenethylamine at room temperature for 12 hours to produce PA-XY13.

16. Phyllanthacidoid aglycone A was dissolved in an organic solvent, and reacted with 367-fold molar equivalents of phenethyl alcohol at room temperature for 12 hours to produce PA-XY14.

17. Phyllanthacidoid aglycone A was dissolved in an organic solvent, and reacted with 20-fold molar equivalents of ethoxypropylamine at room temperature for 12 hours to produce PA-XY15.

18. Phyllanthacidoid aglycone A was dissolved in an organic solvent, and reacted with 367-fold molar equivalents of ethoxypropanol at room temperature for 12 hours to produce PA-XY16.

19. Phyllanthacidoid aglycone A was dissolved in an organic solvent, and reacted with 20-fold molar equivalents of isopropoxypropylamine at room temperature for 12 hours to produce PA-XY17.

20. Phyllanthacidoid aglycone A was dissolved in an organic solvent, and reacted with 367-fold molar equivalents of isopropoxypropanol at room temperature for 12 hours to produce PA-XY18.

21. Phyllanthacidoid aglycone A was dissolved in an organic solvent, and reacted with 20-fold molar equivalents of n-hexylamine at room temperature for 12 hours to produce PA-XY19.

22. Phyllanthacidoid aglycone B was dissolved in an organic solvent, and reacted with 367-fold molar equivalents of n-hexanol at room temperature for 12 hours to produce PA-XY20.

23. Phyllanthacidoid aglycone B was dissolved in an organic solvent, and reacted with 20-fold molar equivalents of n-heptylamine at room temperature for 12 hours to produce PA-XY21.

24. Phyllanthacidoid aglycone B was dissolved in an organic solvent, and reacted with 367-fold molar equivalents of n-heptanol at room temperature for 12 hours to produce PA-XY22.

25. Phyllanthacidoid aglycone B was dissolved in an organic solvent, and reacted with 20-fold molar equivalents of n-octylamine at room temperature for 12 hours to produce YHY23.

26. Phyllanthacidoid aglycone B was dissolved in an organic solvent, and reacted with 367-fold molar equivalents of n-octanol at room temperature for 12 hours to produce PA-XY24.

27. Phyllanthacidoid aglycone B was dissolved in an organic solvent, and reacted with 20-fold molar equivalents of phenethylamine at room temperature for 12 hours to produce PA-XY25.

28. Phyllanthacidoid B was dissolved in an organic solvent, and reacted with 367-fold molar equivalents of phenethyl alcohol at room temperature for 12 hours to produce PA-XY26.

29. Phyllanthacidoid aglycone B was dissolved in an organic solvent, and reacted with 20-fold molar equivalents of ethoxypropylamine at room temperature for 12 hours to produce PA-XY27.

30. Phyllanthacidoid aglycone B was dissolved in an organic solvent, and reacted with 367-fold molar equivalents of ethoxypropanol at room temperature for 12 hours to produce PA-XY28.

31. Phyllanthacidoid aglycone B was dissolved in an organic solvent, and reacted with 20-fold molar equivalents of isopropoxypropylamine at room temperature for 12 hours to produce PA-XY29.

32. Phyllanthacidoid aglycone B was dissolved in an organic solvent, and reacted with 367-fold molar equivalents of isopropoxypropanol at room temperature for 12 hours to produce PA-XY30.

In the above steps, the unspecified ratios are molar ratios.

The substantive content of the present invention is described in detail with examples according to the present invention, which are not intended to limit the present invention in any way. Any modifications or replacements based on the present invention are belonged to the protection scope of the present invention.

Example 1: Synthesis of PA-XY1

Step (1): Approximately 10 mg of phyllanthacidoid A (phyllanthusol A, PA) was placed in a reaction tube, and 1 ml of 0.72 M potassium carbonate solution was added, after dissolving, the mixture was placed in an oil bath at 60° C. and stirred magnetically for two hours to react until the raw materials disappeared. The solution was neutralized with 1M hydrochloric acid to have a pH value of about 2. The solution was added with a certain amount of saline solution to reach a volume of about 4.5 ml, and extracted with 4.5×3 ml of ethyl acetate. Then, the organic phases were collected to evaporate the solvent, so as to obtain a product; Step (2): 10 mg of the product obtained in Step (1) was weighed and dissolved in 1 ml of DMF dried through 3 A molecular sieve, and then added into a reaction tube. 20-fold molar equivalents of n-amylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain PA-XY1, with a yield of about 51%.

Spectrum data of PA-XY1: ESI-MS: m/z 508 [M+H]$^+$; $^1$H NMR (600 MHz, MeOD) δ 7.86 (ddd, J=8.8, 2.7, 2.0 Hz, 2H, H-16, H-20), 6.73 (ddd, J=8.8, 2.7, 2.0 Hz, 2H, H-17, H-19), 5.12 (brd, J=2.6 Hz, 1H, H-10), 4.01 (t, J=3.2 Hz, 1H, H-5), 3.93 (t, J=11.4 Hz, 1H, H-12a), 3.79 (dd, J=10.5, 5.6 Hz, 1H, H-1), 3.65 (s, 1H, H-7), 3.49 (dd, J=11.1, 4.5 Hz, 1H, H-12b), 3.01-2.92 (m, 2H, H-1'), 2.33 (ddd, J=15.1, 11.3, 5.6 Hz, 1H, H-3), 2.10-2.03 (m, 1H, H-9a), 2.02-1.95 (m, 2H, H-11, H-9b), 1.88 (ddd, J=14.6, 11.7, 3.2 Hz, 1H, H-2a), 1.69 (dt, J=14.0, 5.7 Hz, 1H, H-4a), 1.59 (ddd, J=14.4, 5.3, 3.5 Hz, 1H, H-4b), 1.46 (dt, J=13.9, 9.8 Hz, 1H, H-2b), 1.31 (dt, J=14.8, 7.2 Hz, 2H, H-2'), 1.25-1.17 (m, 2H, H-3'), 1.16-1.09 (m, 2H, H-4'), 0.79 (t, J=7.3 Hz, 3H, H-5'), 0.78 (d, J=6.9 Hz, 3H, H-13).

Example 2: Synthesis of PA-XY2

Step (1): 10 mg of phyllanthacidoid B (phyllanthusol B, PB) was placed in a reaction tube, and 1 ml of 0.72 M potassium carbonate solution was added, after dissolving, the mixture was placed in an oil bath at 60° C. and stirred magnetically for two hours to react until the raw materials disappeared. The solution was neutralized with 1M hydrochloric acid to have a pH value of about 2. The solution was added with a certain amount of saline solution to reach a volume of about 4.5 ml, and extracted with 4.5×3 ml of ethyl acetate. Then, the organic phases were collected to evaporate the solvent, so as to obtain a product; Step (2): 10 mg of the product obtained in Step (1) was weighed and dissolved in 1 ml of DMF dried through 3 A molecular sieve, and then added into a reaction tube. 20-fold molar equivalents of n-amylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain PA-XY2, with a yield of about 44%.

Spectrum data of PA-XY2: ESI-MS: m/z 514 [M+Na]$^+$; $^1$H NMR (600 MHz, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.18 (brd, J=2.6 Hz, 1H, H-10), 4.02 (t, J=3.3 Hz, 1H, H-5), 3.95 (t, J=11.4 Hz, 1H, H-12a), 3.79 (dd, J=10.5, 5.5 Hz, 1H, H-1), 3.65 (s, 1H, H-7), 3.51 (dd, J=11.1, 4.4 Hz, 1H, H-12b), 3.00-2.89 (m, 2H, H-1'), 2.33 (ddd, J=15.1, 11.3, 5.6 Hz, 1H, H-3), 2.09 (dd, J=14.8, 3.2 Hz, 1H, H-9a), 2.05-1.97 (m, 2H, H-11, H-9b), 1.89 (ddd, J=14.7, 11.6, 3.3 Hz, 1H, H-2a), 1.68 (dt, J=14.0, 5.6 Hz, 1H, H-4a), 1.58 (ddd, J=14.4, 5.4, 3.6 Hz, 1H, H-4b), 1.47 (dt, J=14.0, 9.9 Hz, 1H, H-2b), 1.30 (dt, J=14.4, 7.2 Hz, 2H, H-2'), 1.24-1.17 (m, 2H, H-3'), 1.12 (tdd, J=9.6, 7.0, 3.7 Hz, 2H, H-4'), 0.80 (t, J=7.2 Hz, 3H, H-5'), 0.79 (d, J=7.2 Hz, 3H, H-13).

Example 3: Synthesis of PA-XY7

The product obtained in Step (1) of Example 1 (10 mg of PA, as row material, was used) was dissolved in 1 to 1.5 ml of DMF dried through 3 A molecular sieve, and then added into a reaction tube. 20-fold molar equivalents of n-hexylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 60%.

Spectrum data of PA-XY7: ESI-MS: m/z 544 [M+Na]$^+$, $^1$H NMR (600 MHz, MeOD) δ 7.94 (brd, J=8.7 Hz, 2H, H-16, H-20), 6.81 (brd, J=8.7 Hz, 2H, H-17, H-19), 5.21 (brd, J=1.9 Hz, 1H, H-10), 4.09 (t, J=2.9 Hz, 1H, H-5), 4.02 (t, J=11.4 Hz, 1H, H-12a), 3.88 (dd, J=10.5, 5.6 Hz, 1H, H-1), 3.73 (s, 1H, H-7), 3.59 (dd, J=11.2, 4.5 Hz, 1H, H-12b), 3.05 (td, J=7.1, 2.6 Hz, 2H, H-1'), 2.37-2.29 (m, 1H, H-3), 2.15 (dd, J=14.8, 3.0 Hz, 1H, H-9a), 2.11-2.02 (m, 2H, H-11, H-9b), 2.00-1.93 (m, 1H, H-2a), 1.78 (dt, J=13.8, 5.7 Hz, 1H, H-4a), 1.71-1.64 (m, 1H, H-4b), 1.55 (dt, J=13.9, 10.0 Hz, 1H, H-2b), 1.42-1.36 (m, 2H, H-2'), 1.35-1.21 (m, 6H, H-3', H-4', H-5'), 0.92-0.84 (m, 6H, H-6', H-13).

Example 4: Synthesis of PA-XY9

The product obtained in Step (1) of Example 1 (10 mg of PA, as row material, was used) was dissolved in 1 to 1.5 ml of DMF dried through 3 A molecular sieve, and then added into a reaction tube. 20-fold molar equivalents of heptamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 71%.

Spectrum data of PA-XY9: ESI-MS: m/z 572 [M+Na]$^+$, $^1$H NMR (600 MHz, MeOD) δ 7.94 (brd, J=8.7 Hz, 2H, H-16, H-20), 6.80 (brd, J=8.7 Hz, 2H, H-17, H-19), 5.21 (brs, 1H, H-10), 4.09 (brs, 1H, H-5), 4.02 (t, J=11.4 Hz, 1H, H-12a), 3.88 (dd, J=10.4, 5.6 Hz, 1H, H-1), 3.73 (s, 1H, H-7), 3.59 (dd, J=11.1, 4.2 Hz, 1H, H-12b), 3.05 (t, J=7.0 Hz, 1H, H-1'), 2.41 (dq, J=16.2, 5.5 Hz, 1H, H-3), 2.15 (dd, J=14.7, 2.9 Hz, 1H, H-9a), 2.07 (dd, J=14.8, 2.4 Hz, 2H, H-11, H-9b), 2.00-1.92 (m, 1H, H-2a), 1.78 (dt, J=13.7, 5.6 Hz, 1H, H-4a), 1.72-1.64 (m, 1H, H-4b), 1.55 (dt, J=13.8, 10.0 Hz, 1H, H-2a), 1.40 (dd, J=14.0, 7.0 Hz, 2H, H-2'), 1.35-1.20 (m, 10H, H-3', H-4', H-5', H-6', H-7'), 0.95-0.83 (m, 6H, H-13, H-8').

Example 5: Synthesis of PA-XY11

The product obtained in Step (1) of Example 1 (10 mg of PA, as row material, was used) was dissolved in 1 to 1.5 ml of DMF dried through 3 A molecular sieve, and then added into a reaction tube. 20-fold molar equivalents of octylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 65%.

Spectrum data of PA-XY11: ESI-MS: m/z 536 [M+H]$^+$, $^1$H NMR (600 MHz, MeOD) δ 7.93 (brd, J=8.8 Hz, 2H, H-16, H-20), 6.79 (brd, J=8.8 Hz, 2H, H-17, H-19), 5.21 (brd, J=2.2 Hz, 1H, H-10), 4.09 (t, J=3.1 Hz, 1H, H-5), 4.02 (t, J=11.4 Hz, 1H, H-12a), 3.88 (dd, J=10.5, 5.6 Hz, 1H, H-1), 3.73 (s, 1H, H-7), 3.58 (dd, J=11.0, 4.5 Hz, 1H, H-12b), 3.05 (t, J=7.1 Hz, 2H, H-1'), 2.48-2.37 (m, 1H, H-3), 2.17-2.11 (m, 1H, H-9a), 2.12-2.03 (m, 2H, H-11, H-9b), 2.01-1.92 (m, 1H, H-2a), 1.78 (dt, J=13.9, 5.6 Hz, 1H, H-4a), 1.68 (ddd, J=14.4, 5.2, 3.6 Hz, 1H, H-4b), 1.62-1.50 (m, 1H, H-2a), 1.39 (dq, J=14.2, 7.1 Hz, 2H, H-2'), 1.36-1.18 (m, 8H, H-3', H-4', H-5', H-6'), 0.94-0.82 (m, 6H, H-7', H-13).

Example 6: Synthesis of PA-XY13

The product obtained in Step (1) of Example 1 (10 mg of PA, as row material, was used (1-fold molar equivalent)) was dissolved in 1 to 1.5 ml of DMF dried through 3 A molecular sieve, and then added into a reaction tube. 20-fold molar equivalents of phenethylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 74%.

Spectrum data of PA-XY13: ESI-MS: m/z 564 [M+Na]$^+$, $^1$H NMR (600 MHz, MeOD) δ 7.94 (brd, J=8.7 Hz, 2H, H-16, H-20), 7.22 (t, J=7.4 Hz, 2H, H-3', H-5'), 7.18-7.12 (m, 3H, H-2', H-4', H-6'), 6.82 (brd, J=8.7 Hz, 2H, H-17, H-19), 5.20 (brs, 1H, H-10), 4.08 (brs, 1H, H-5), 4.01 (t, J=11.4 Hz, 1H, H-12a), 3.86 (dd, J=10.5, 5.5 Hz, 1H, H-1), 3.72 (s, 1H, H-7), 3.58 (dd, J=11.0, 4.2 Hz, 1H, H-12b), 3.36-3.24 (m, 4H, H-8', overlap with methanol), 2.69 (t, J=7.3 Hz, 2H, H-7'), 2.37 (dq, J=16.2, 5.4 Hz, 1H, H-3), 2.14 (dd, J=14.7, 2.9 Hz, 1H, H-9a), 2.11-2.01 (m, 2H, H-11, H-9b), 1.96-1.87 (m, 1H, H-2a), 1.75 (dt, J=13.7, 5.5 Hz, 1H, H-4a), 1.68-1.62 (m, 1H, H-4b), 1.51 (dt, J=13.8, 10.1 Hz, 1H, H-2b), 0.87 (d, J=6.9 Hz, 3H, H-13).

Example 7: Synthesis of PA-XY15

The product obtained in Step (1) of Example 1 (10 mg of PA, as row material, was used (1-fold molar equivalent)) was dissolved in 1 to 1.5 ml of DMF dried through 3 A molecular sieve, and then added into a reaction tube. 20-fold molar equivalents of ethoxypropylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 61%.

Spectrum data of PA-XY15: $^1$H NMR (600 MHz, MeOD) δ 7.95 (brd, J=8.8 Hz, 2H, H-16, H-20), 6.81 (brd, J=8.8 Hz, 2H, H-17, H-19), 5.21 (brd, J=2.2 Hz, 1H, H-10), 4.09 (t, J=3.1 Hz, 1H, H-5), 4.02 (t, J=11.4 Hz, 1H, H-12a), 3.88 (dd, J=10.5, 5.6 Hz, 1H, H-1), 3.74 (s, 1H, H-7), 3.59 (dd, J=11.1, 4.5 Hz, 1H, H-12b), 3.56-3.49 (m, 1H, H-4'), 3.39 (t, J=6.2 Hz, 2H, H-3'), 3.20-3.10 (m, 1H, H-1'), 2.41 (qd, J=11.2, 5.6 Hz, 1H, H-3), 2.15 (dd, J=14.8, 3.1 Hz, 1H, H-9a), 2.11-2.03 (m, 1H, H-11, H-9b), 2.01-1.94 (m, 1H, H-2a), 1.78 (dt, J=13.9, 5.7 Hz, 1H, H-4a), 1.72-1.60 (m, 3H, H-4b, H-2'), 1.56 (dt, J=13.9, 9.9 Hz, 1H, H-2a), 1.10 (dd, J=6.1, 3.4 Hz, 6H, H-5', H-6'), 0.87 (d, J=6.9 Hz, 3H, H-13).

Example 8: Synthesis of PA-XY17

The product obtained in Step (1) of Example 1 (10 mg of PA, as row material, was used (1-fold molar equivalent)) was dissolved in 1 to 1.5 ml of DMF dried through 3 A molecular sieve, and then added into a reaction tube. 20-fold molar equivalents of isopropoxypropylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 60%.

Spectrum data of PA-XY17: ESI-MS: m/z 546 [M+Na]$^+$, $^1$H NMR (600 MHz, MeOD) δ 7.95 (brd, J=8.7 Hz, 2H, H-16, H-20), 6.81 (brd, J=8.7 Hz, 2H, H-17, H-19), 5.21 (brs, 1H, H-10), 4.10 (brs, 1H, H-5), 4.02 (t, J=11.4 Hz, 1H, H-12a), 3.88 (dd, J=10.4, 5.6 Hz, 1H, H-1), 3.74 (s, 1H, H-7), 3.59 (dd, J=10.9, 4.2 Hz, 1H, H-12b), 3.43 (q, J=7.0 Hz, 2H, H-4'), 3.38 (t, J=6.2 Hz, 1H, H-3'), 3.15 (ddq, J=20.3, 13.5, 6.9 Hz, 2H, H-1'), 2.41 (tt, J=11.1, 5.5 Hz, 1H, H-3), 2.14 (dt, J=10.5, 5.3 Hz, 1H, H-9a), 2.11-2.03 (m, 2H, H-11, H-9b), 2.00-1.93 (m, 1H, H-2a), 1.79 (dt, J=13.7, 5.6 Hz, 1H, H-4a), 1.72-1.62 (m, 3H, H-4b, H-2'), 1.56 (dt, J=13.8, 10.0 Hz, 1H, H-2b), 1.14 (t, J=7.0 Hz, 3H, H-5'), 0.87 (d, J=6.9 Hz, 3H, H-13).

Example 9: Synthesis of PA-XY19

The product obtained in Step (1) of Example 2 (10 mg of PB, as row material, was used (1-fold molar equivalent)) was dissolved in 1 to 1.5 ml of DMF dried through 3 A molecular sieve, and then added into a reaction tube. 20-fold molar equivalents of n-hexylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 60%.

Spectrum data of PA-XY19: ESI-MS: 528 [M+Na]$^+$, $^1$H NMR (600 MHz, MeOD) 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.21 (brd, J=1.9 Hz, 1H, H-10), 4.09 (t, J=2.9 Hz, 1H, H-5), 4.02 (t, J=11.4 Hz, 1H, H-12a), 3.88 (dd, J=10.5, 5.6 Hz, 1H, H-1), 3.73 (s, 1H, H-7), 3.59 (dd, J=11.2, 4.5 Hz, 1H, H-12b), 3.05 (td, J=7.1, 2.6 Hz, 2H, H-1'), 2.37-2.29 (m, 1H, H-3), 2.15 (dd, J=14.8, 3.0 Hz, 1H, H-9a), 2.11-2.02 (m, 2H, H-11, H-9b), 2.00-1.93 (m, 1H, H-2a), 1.78 (dt, J=13.8, 5.7 Hz, 1H, H-4a), 1.71-1.64 (m, 1H, H-4b), 1.55 (dt, J=13.9, 10.0 Hz, 1H, H-2b), 1.42-1.36 (m, 2H, H-2'), 1.35-1.21 (m, 6H, H-3', H-4', H-5'), 0.92-0.84 (m, 6H, H-6', H-13).

Example 10: Synthesis of PA-XY21

The product obtained in Step (1) of Example 2 (10 mg of PB, as row material, was used (1-fold molar equivalent)) was dissolved in 1 to 1.5 ml of DMF dried through 3 A molecular sieve, and then added into a reaction tube. 20-fold molar equivalents of heptamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 71%.

Spectrum data of PA-XY21: ESI-MS: m/z 556 [M+Na]$^+$, $^1$H NMR (600 MHz, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.21 (brs, 1H, H-10), 4.09 (brs, 1H, H-5), 4.02 (t, J=11.4 Hz, 1H, H-12a), 3.88 (dd, J=10.4, 5.6 Hz, 1H, H-1), 3.73 (s, 1H, H-7), 3.59 (dd, J=11.1, 4.2 Hz, 1H, H-12b), 3.05 (t, J=7.0 Hz, 1H, H-1'), 2.41 (dq, J=16.2, 5.5 Hz, 1H, H-3), 2.15 (dd, J=14.7, 2.9 Hz, 1H, H-9a), 2.07 (dd, J=14.8, 2.4 Hz, 2H, H-11, H-9b), 2.00-1.92 (m, 1H, H-2a), 1.78 (dt, J=13.7, 5.6 Hz, 1H, H-4a), 1.72-1.64 (m, 1H, H-4b), 1.55 (dt, J=13.8, 10.0 Hz, 1H, H-2a), 1.40 (dd, J=14.0, 7.0 Hz, 2H, H-2'), 1.35-1.20 (m, 10H, H-3', H-4', H-5', H-6', H-7'), 0.95-0.83 (m, 6H, H-13, H-8').

Example 11: Synthesis of PA-XY23

The product obtained in Step (1) of Example 2 (10 mg of PB, as row material, was used (1-fold molar equivalent)) was dissolved in 1 to 1.5 ml of DMF dried through 3 A molecular sieve, and then added into a reaction tube. 20-fold molar equivalents of octylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 65%.

Spectrum data of PA-XY23: ESI-MS: m/z 520 [M+H]$^+$, H NMR (600 MHz, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.21 (brd, J=2.2 Hz, 1H, H-10), 4.09 (t, J=3.1 Hz, 1H, H-5), 4.02 (t, J=11.4 Hz, 1H, H-12a), 3.88 (dd, J=10.5, 5.6 Hz, 1H, H-1), 3.73 (s, 1H, H-7), 3.58 (dd, J=11.0, 4.5 Hz, 1H, H-12b), 3.05 (t, J=7.1 Hz, 2H, H-1'), 2.48-2.37 (m, 1H, H-3), 2.17-2.11 (m, 1H, H-9a), 2.12-2.03 (m, 2H, H-11, H-9b), 2.01-1.92 (m, 1H, H-2a), 1.78 (dt, J=13.9, 5.6 Hz, 1H, H-4a), 1.68 (ddd, J=14.4, 5.2, 3.6 Hz, 1H, H-4b), 1.62-1.50 (m, 1H, H-2a), 1.39 (dq, J=14.2, 7.1 Hz, 2H, H-2'), 1.36-1.18 (m, 8H, H-3', H-4', H-5', H-6'), 0.94-0.82 (m, 6H, H-7', H-13).

Example 12: Synthesis of PA-XY25

The product obtained in Step (1) of Example 2 (10 mg of PB, as row material, was used (1-fold molar equivalent)) was dissolved in 1 to 1.5 ml of DMF dried through 3 A molecular sieve, and then added into a reaction tube. 20-fold molar equivalents of phenethylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 74%.

Spectrum data of PA-XY25: ESI-MS: m/z 548 [M+Na]$^+$, $^1$H NMR (600 MHz, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 6.82 (brd, J=8.7 Hz, 2H, H-17, H-19), 5.20 (brs, 1H, H-10), 4.08 (brs, 1H, H-5), 4.01 (t, J=11.4 Hz, 1H, H-12a), 3.86 (dd, J=10.5, 5.5 Hz, 1H, H-1), 3.72 (s, 1H, H-7), 3.58 (dd, J=11.0, 4.2 Hz, 1H, H-12b), 3.36-3.24 (m, 4H, H-8', overlap with methanol), 2.69 (t, J=7.3 Hz, 2H, H-7'), 2.37 (dq, J=16.2, 5.4 Hz, 1H, H-3), 2.14 (dd, J=14.7, 2.9 Hz, 1H, H-9a), 2.11-2.01 (m, 2H, H-11, H-9b), 1.96-1.87 (m, 1H, H-2a), 1.75 (dt, J=13.7, 5.5 Hz, 1H, H-4a), 1.68-1.62 (m, 1H, H-4b), 1.51 (dt, J=13.8, 10.1 Hz, 1H, H-2b), 0.87 (d, J=6.9 Hz, 3H, H-13).

Example 13: Synthesis of PA-XY27

The product obtained in Step (1) of Example 2 (10 mg of PB, as row material, was used (1-fold molar equivalent)) was dissolved in 1 to 1.5 ml of DMF dried through 3 A molecular sieve, and then added into a reaction tube. 20-fold molar equivalents of ethoxypropylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 61%.

Spectrum data of PA-XY27: $^1$H NMR (600 MHz, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.21 (brd, J=2.2 Hz, 1H, H-10), 4.09 (t, J=3.1 Hz, 1H, H-5), 4.02 (t, J=11.4 Hz, 1H, H-12a), 3.88 (dd, J=10.5, 5.6 Hz, 1H, H-1), 3.74 (s, 1H, H-7), 3.59 (dd, J=11.1, 4.5 Hz, 1H, H-12b), 3.56-3.49 (m, 1H, H-4'), 3.39 (t, J=6.2 Hz, 2H, H-3'), 3.20-3.10 (m, 1H, H-1'), 2.41 (qd, J=11.2, 5.6 Hz, 1H, H-3), 2.15 (dd, J=14.8, 3.1 Hz, 1H, H-9a), 2.11-2.03 (m, 1H, H-11, H-9b), 2.01-1.94 (m, 1H, H-2a), 1.78 (dt, J=13.9, 5.7 Hz, 1H, H-4a), 1.72-1.60 (m, 3H, H-4b, H-2'), 1.56 (dt, J=13.9, 9.9 Hz, 1H, H-2a), 1.10 (dd, J=6.1, 3.4 Hz, 6H, H-5', H-6'), 0.87 (d, J=6.9 Hz, 3H, H-13).

Example 14: Synthesis of PA-XY29

The product obtained in Step (1) of Example 2 (10 mg of PB, as row material, was used (1-fold molar equivalent)) was dissolved in 1 to 1.5 ml of DMF dried through 3 A molecular sieve, and then added into a reaction tube. 20-fold molar equivalents of isopropoxypropylamine, 10 times molar equivalent of HOSU, EDCI and 2 times molar equivalent of DMAP were added and reacted overnight at room temperature, while the reaction of the raw materials was monitored by TLC. The reaction was usually finished after 12 hours. After the reaction was complete, the reaction solution was added with 10% citric acid to 4-5 ml, and extracted with 5×3 ml of ethyl acetate. The organic phases were combined, concentrated, and then dissolved again with about 7 ml of dichloromethane. If precipitation occurred, a very small amount of methanol was added to increase the solubility (methanol content is less than 5%), the solution was separated and purified by amino silica gel to obtain a product, with a yield of about 60%.

Spectrum data of PA-XY29: ESI-MS: m/z 530 [M+Na]$^+$, $^1$H NMR (600 MHz, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.21 (brs, 1H, H-10), 4.10 (brs, 1H, H-5), 4.02 (t, J=11.4 Hz, 1H, H-12a), 3.88 (dd, J=10.4, 5.6 Hz, 1H, H-1), 3.74 (s, 1H, H-7), 3.59 (dd, J=10.9, 4.2 Hz, 1H, H-12b), 3.43 (q, J=7.0 Hz, 2H, H-4'), 3.38 (t, J=6.2 Hz, 1H, H-3'), 3.15 (ddq, J=20.3, 13.5, 6.9 Hz, 2H, H-1'), 2.41 (tt, J=11.1, 5.5 Hz, 1H, H-3), 2.14 (dt, J=10.5, 5.3 Hz, 1H, H-9a), 2.11-2.03 (m, 2H, H-11, H-9b), 2.00-1.93 (m, 1H, H-2a), 1.79 (dt, J=13.7, 5.6 Hz, 1H, H-4a), 1.72-1.62 (m, 3H, H-4b, H-2'), 1.56 (dt, J=13.8, 10.0 Hz, 1H, H-2b), 1.14 (t, J=7.0 Hz, 3H, H-5'), 0.87 (d, J=6.9 Hz, 3H, H-13).

Example 15: In Vitro Assays of Anti-Hepatitis B Virus Activity

Materials and methods: In vitro cell model: HepG2 2.215 cells; antigen inhibition of samples was detected with Elaisa method; positive control: Lamivudine.

Procedure of assay: preparation of medicament solutions: the medicament was first dissolved with DMSO to prepare a concentrated solution (40 mg/mL), and the concentrated solution was diluted with cell culture medium to prepare five concentrations of 200 μg/mL, 100 μg/mL, 50 μg/mL, 25 μg/mL, and 12.5 μg/mL before the assays; cytotoxicity assay of the medicament: HepG2 2.2.15 cells were incubated in a 96-well cell culture plate for 48 hours, then the plate was added with the above-mentioned culture media having different medicament concentrations, the cells were further incubated for 9 days, during which the medium was changed every 3 days, and then the toxicity of the medicament on HepG2 2.2.15 cells was observed.

Detection of HBV virus inhibitory effect of medicament: HepG2 2.2.15 cells were incubated in a 24-well cell culture plate for 48 hours, then the plate was added with the above-mentioned culture media having different medicament concentrations, and the cells were further incubated for 9 days, during which the medium was changed every 3 days.

Figure 1:
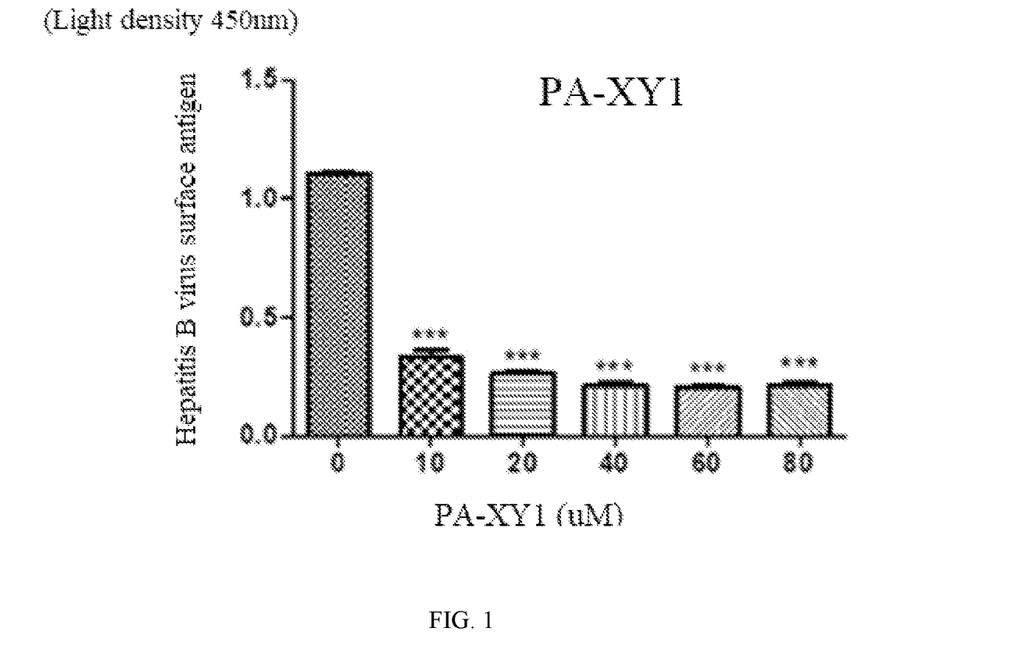
FIG. 1 is a schematic diagram of an inhibitory activity of phyllanthacidoid pentane amide PA-XY1 against hepatitis B virus surface antigen in a cell model.
Figure 2:
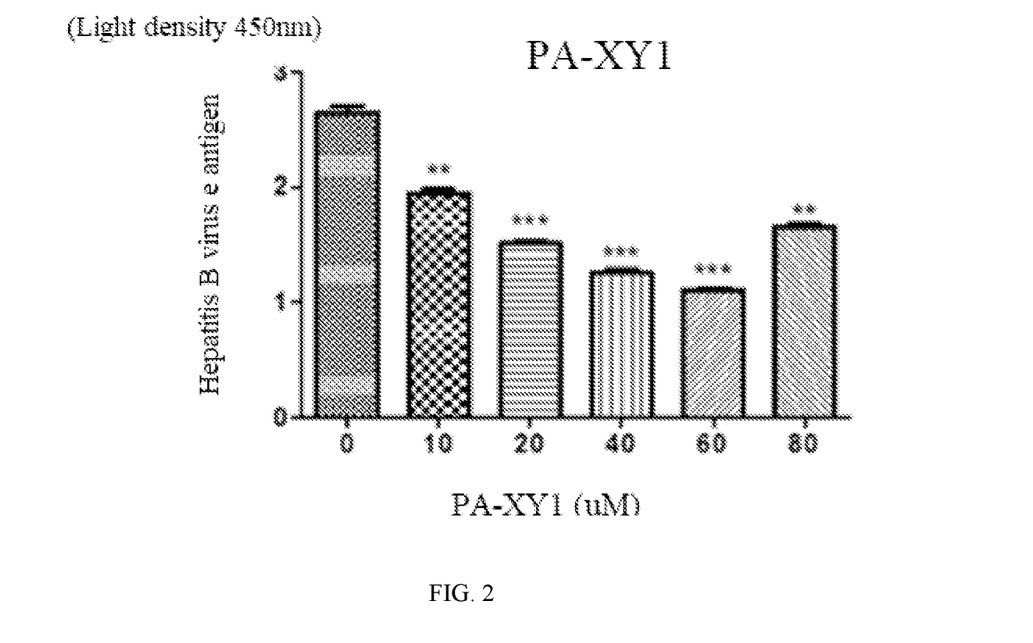
FIG. 2 is a schematic diagram of an inhibitory activity of phyllanthacidoid pentane amide PA-XY1 against anti-hepatitis B virus e antigen in a cell model.
Figure 3:
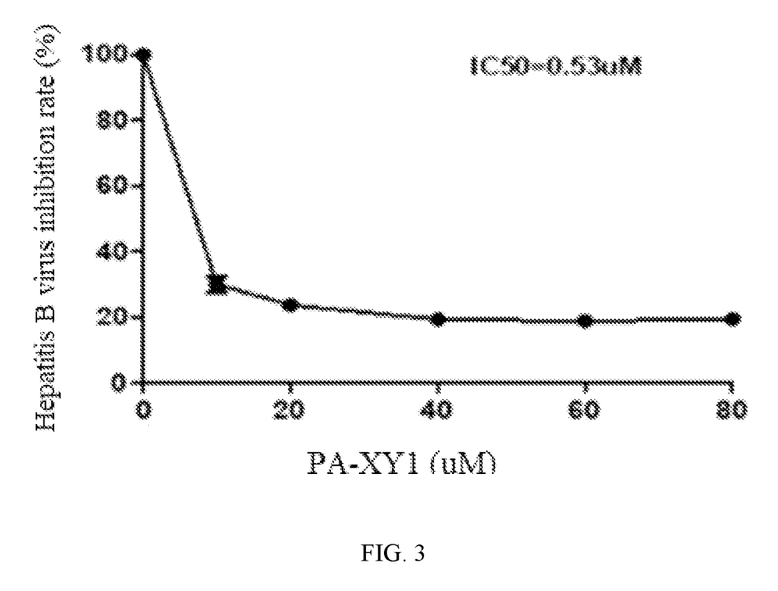
FIG. 3 is a schematic diagram of an anti-hepatitis B virus activity of phyllanthacidoid pentane amide PA-XY1 in a cell model.
Figure 4:
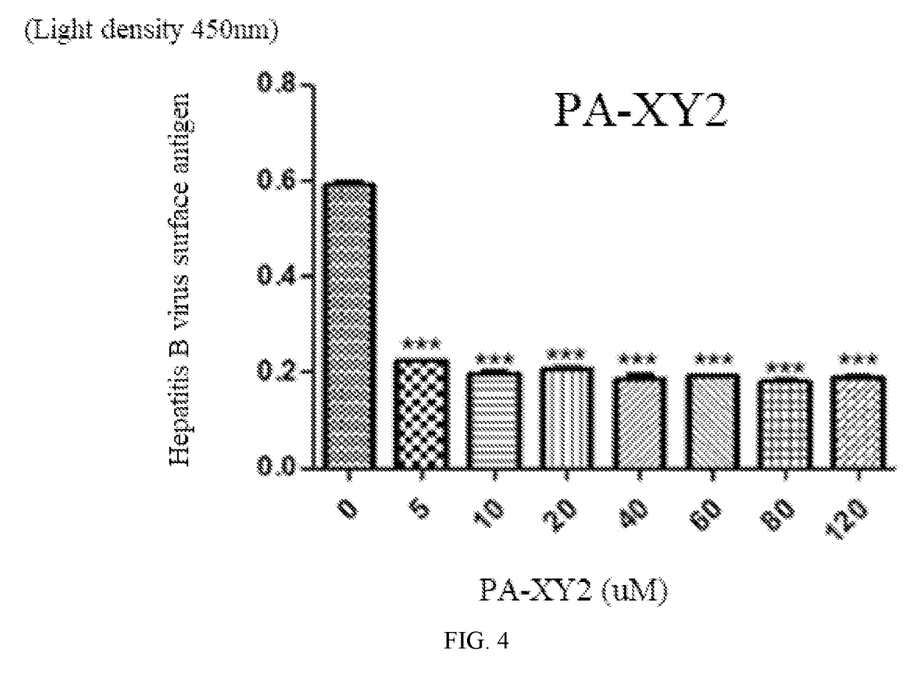
FIG. 4 is a schematic diagram of an inhibitory activity of phyllanthacidoid pentane amide PA-XY2 on hepatitis B virus surface antigen in a cell model.
Figure 5:
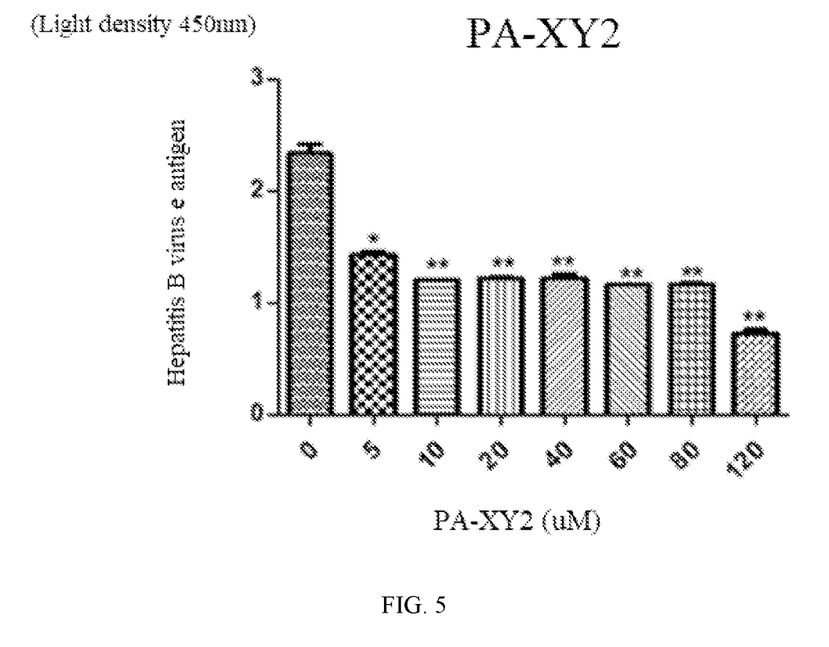
FIG. 5 is a schematic diagram of an inhibitory activity of phyllanthacidoid pentane amide PA-XY2 on hepatitis B virus e antigen in a cell model.
Figure 6:
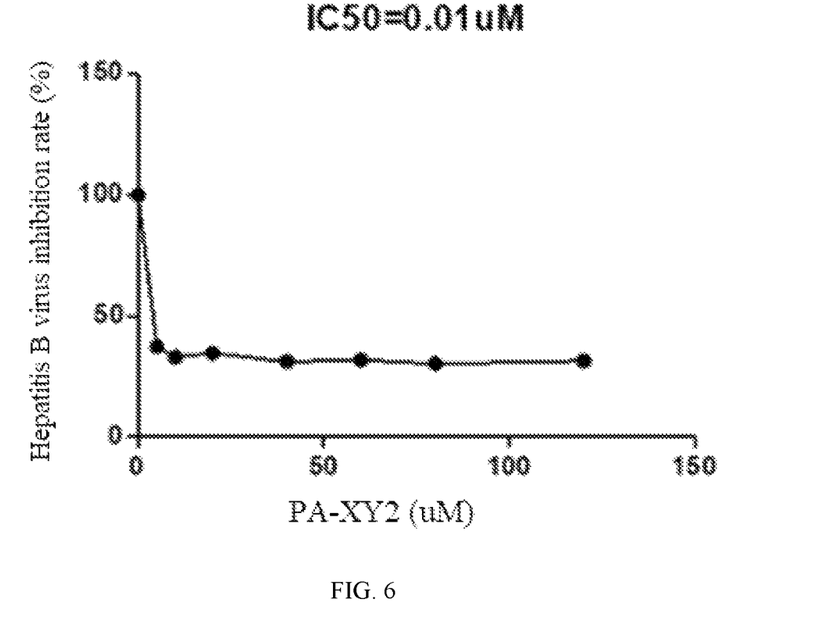
FIG. 6 is a schematic diagram of an anti-hepatitis B virus activity of phyllanthacidoid pentane amide PA-XY2 in a cell model.

Then, the supernatant was collected, and the inhibitory effects of the samples on HBV surface antigen and e antigen were detected with ELISA. The results are shown in Table 1 below. As shown in FIGS. 1, 2 and 3, PA-XY1 significantly inhibited the hepatitis B virus surface antigen (FIG. 1) as well as the e antigen (FIG. 2), with a half-inhibition concentration of 530 nM (FIG. 3). As shown in FIGS. 4, 5 and 6, PA-XY2 also significantly inhibited the hepatitis B virus surface antigen (FIG. 4) as well as the e antigen (FIG. 5), with a half-inhibition rate of 10 nM (FIG. 6).

TABLE 1

| Sample No. | $IC_{50}$ (µM) | TC50 | SI |
|---|---|---|---|
| PA-XY1 | 0.53 | >500 µM | >943 |
| PA-XY2 | 0.01 | >500 µM | >50000 |
| PA-XY3 | 10.61 | >500 µM | >47 |
| PA-XY4 | 28.44 | >500 µM | >18 |
| PA-XY5 | 13.87 | >500 µM | >36 |
| PA-XY6 | 16.09 | >500 µM | >31 |
| PA-XY7 | 17.05 | >500 µM | >29 |
| PA-XY8 | 31.13 | >500 µM | >16 |
| PA-XY9 | 15.08 | >500 µM | >33 |
| PA-XY10 | 40.32 | >500 µM | >12 |
| PA-XY11 | 9.31 | >500 µM | >53 |
| PA-XY12 | 23.06 | >500 µM | >21 |
| PA-XY13 | 14.81 | >500 µM | >34 |
| PA-XY14 | 35.26 | >500 µM | >14 |
| PA-XY15 | 28.44 | >500 µM | >18 |
| PA-XY16 | 52.10 | >500 µM | >10 |
| PA-XY17 | 47.66 | >500 µM | >10 |
| PA-XY18 | 76.10 | >500 µM | >6 |
| PA-XY19 | 1.75 | >500 µM | >286 |
| PA-XY20 | 3.13 | >500 µM | >159 |
| PA-XY21 | 1.51 | >500 µM | >331 |
| PA-XY22 | 4.38 | >500 µM | >114 |
| PA-XY23 | 0.93 | >500 µM | >537 |
| PA-XY24 | 3.06 | >500 µM | >163 |
| PA-XY25 | 1.48 | >500 µM | >337 |
| PA-XY26 | 3.53 | >500 µM | >174 |
| PA-XY27 | 2.87 | >500 µM | >174 |
| PA-XY28 | 10.09 | >500 µM | >49 |
| PA-XY29 | 7.84 | >500 µM | >64 |

Example 16: In Vivo Assays of Anti-Hepatitis B Virus Activity

Experimental materials: 400 µg/ml HBV1.2 plasmid, normal saline; 6-8 weeks old C57 mice, ♂, 20 mice.

Administration method: intragastric administration once a day for one week; dose: HBV1.2 plasmid 10 µg/each mouse, and 0.1 mg/gram of body weight;
  Detection: ① time point: 2 days after the administration
  ② Blood collection: 50 µl
  ③ Method: the mouse blood was centrifugated and the supernatant was separated, HBsAg and HBeAg levels were measured with Elisa; liver tissue section.

Experimental results: The results show that, compared with the model group, the PA-XY1 and PA-XY2 groups and the lamivudine group significantly inhibited the hepatitis B virus at 20 mg/Kg, and the PA-XY1 and PA-XY2 groups were superior to the lamivudine group; HBsAg in serum and liver tissues of mice infected with hepatitis B virus was effectively suppressed without affecting the HBV-DNA level, and the livers were sufficiently protected from hepatitis B virus damage.

Example 17: Research on the Mechanism of Anti-Hepatitis B Virus Effect

Materials and methods: In vitro cell model: HepG2 2.215 cells; and effects of samples on the hepatocyte nuclear factor 4 (HNF-4) were measured with Western blot method.

Procedure of assay: preparation of medicament solutions: the medicament was first dissolved with DMSO to prepare a concentrated solution (40 mg/mL), and the concentrated solution was diluted with cell culture medium to prepare five concentrations of 200 µg/mL, 100 µg/mL, 50 µg/mL, 25 µg/mL, and 12.5 µg/mL before the assays; cytotoxicity assay of the medicament: HepG2 2.2.15 cells were incubated in a 96-well cell culture plate for 48 hours, then the plate was added with the above-mentioned culture media having different medicament concentrations, the cells were further incubated for 9 days, during which the medium was changed every 3 days, and then the toxicity of the medicament on HepG2 2.2.15 cells was observed.

Detection of effect of medicament on HNF-4α: HepG2 2.2.15 cells were incubated in a 24-well cell culture plate for 48 hours, then the plate was added with the above-mentioned culture media having different medicament concentrations, and the cells were further incubated for 9 days, during which the medium was changed every 3 days. Then, the supernatant was collected, and the effects of the samples on the hepatocyte nuclear factor 4 (HNF-4) were measured with Western blot method.

Figure 7:
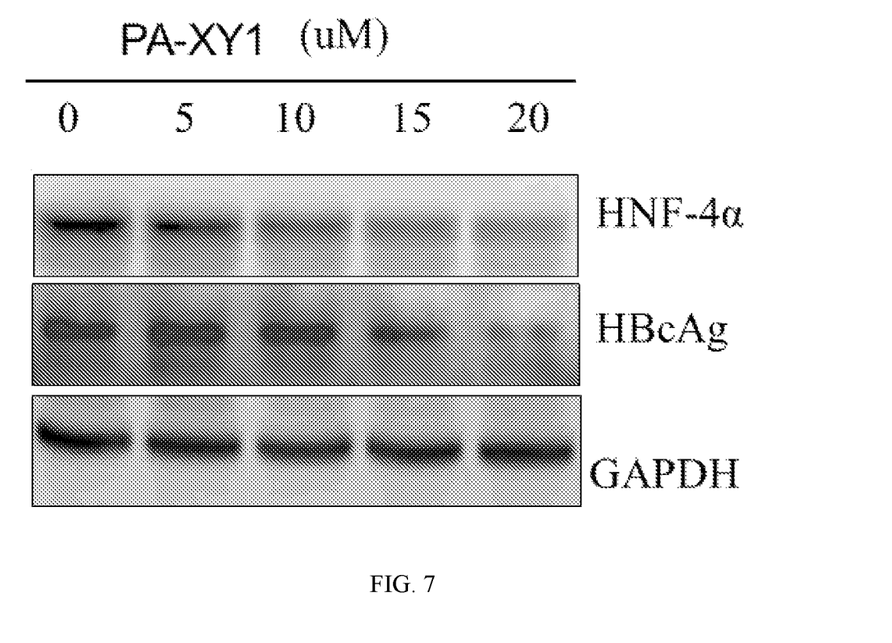
FIG. 7 is a schematic diagram of down-regulation of hepatocyte nuclear factor 4α (HNF-4α) by phyllanthacidoid pentane amide PA-XY1.

The results show that PA-XY1 and PA-XY2 significantly down-regulated the expression of the hepatocyte nuclear factor 4 (HNF-4). As shown in FIG. 7, PA-XY1 significantly down-regulated the expression of the hepatocyte nuclear factor 4 (HNF-4) and the expression of the hepatitis B core antigen (HBc Ag), suggesting that PA-XY1 is a potential medicament having a new mechanism for treating the chronic hepatitis B diseases.

Example 18: Acute Toxicity Assay of PA-XY1

Kunming female mice, 6 to 8 weeks old, weighing 24 to 31 g, were fed with standard feed in a feeding room with an artificial light source (bright for 12 h and dark for 12 h), and water was accessible at any time. Three mice were randomly selected and randomly divided into 3 groups, and the medicament to be tested was administered by intragastric administration at the same time, the solvent was 10% ethanol/saline; doses: 50 mg/kg, ~300 µl, once; 500 mg/kg, ~300 µl, once; 2000 mg/kg. ~900 µl, separately administrated three times, with an interval of 3 h, 300 µl each time. The followings of the mice were observed: skin, coat, eyes, breathing, movement, mental state, mucous membranes, fecal matter, etc. As results, no toxic reaction and no death occurred in the three groups of mice, and the mice were in good condition and gained some weight. Subsequently, four mice were randomly selected to intragastric administrated with the medicament to be tested at a dose of 2000 mg/kg, ~900 µl, separately administrated three times, with an interval of 3 h, 300 µl each time. The mice in the experimental group had no toxic reactions and were in good condition. After the experiments finished, all mice in the experimental group and two other mice (as blank controls) were anesthetized with pentobarbital sodium, ice PBS was perfused through the hearts, the livers were taken and fixed with 4% paraformaldehyde. Pathological sections of the livers show that PA-XY1 and PA-XY2 did not exhibit acute toxicity at a dose of 2000 mg/kg.

Example 19: Preparation of PA-XY1 Tablets 1000 g of PA-XY1 and 100 g of medicinal starch were mixed evenly, granulated with an appropriate amount of ethanol as a binder, then dried, finely granulated by a granulator, compressed to obtain tables, 0.30 g per tablet. The tablets are orally administered, once 1 to 2 tablets, and twice a day.

Example 20: Preparation of PA-XY1 Capsules 1000 g of PA-XY1 and 100 g of medicinal starch were mixed evenly, granulated with an appropriate amount of ethanol as a binder, then dried, finely granulated by a granulator, filled in 0 #capsules, 0.30 g per capsule. The capsules are orally administered, once 1 to 2 capsules, and twice a day.

Example 21: Preparation of PA-XY1 Granules

The PA-XY1 was finely granulated by a granulator, and separately packed. The granules are orally administered, once 5 g, and twice a day.

Example 22: Preparation of PA-XY1 Beverage 100 g of PA-XY1, 1000 ml of food-grade purified water, 500 g of powdered sugar, appropriate amount of stabilizer and flavoring agent were mixed evenly. The beverage can be orally administered, 10 mL each time, twice a day.

Example 23: Preparation of PA-XY2 Tablets 1000 g of PA-XY2 and 100 g of medicinal starch were mixed evenly, granulated with an appropriate amount of ethanol as a binder, then dried, finely granulated by a granulator, compressed to obtain tables, 0.30 g per tablet. The tablets are orally administered, once 1 to 2 tablets, and twice a day.

Example 24: Preparation of PA-XY2 Capsules 1000 g of PA-XY2 and 100 g of medicinal starch were mixed evenly, granulated with an appropriate amount of ethanol as a binder, then dried, finely granulated by a granulator, filled in 0 #capsules, 0.30 g per capsule. The capsules are orally administered, once 1 to 2 capsules, and twice a day.

Example 25: Preparation of PA-XY2 Granules

The PA-XY2 was finely granulated by a granulator, and separately packed. The granules are orally administered, once 5 g, and twice a day.

Example 26: Preparation of PA-XY2 Beverage

100 g of PA-XY2, 1000 ml of food-grade purified water, 500 g of powdered sugar, appropriate amount of stabilizer and flavoring agent were mixed evenly. The beverage can be orally administered, 10 mL each time, twice a day.

What is claimed is:

1. A sesquiterpene derivative, having a structure represented by the following structural formula I, II, III or IV:

wherein in the structural formula I and the structural formula II, $R_1$ is independently selected from the group consisting of benzoate group, p-hydroxybenzoate group, and hydrogen;

in the structural formula III and the structural formula IV, $R_1$ is independently selected from n-hexylamino, n-heptylamino, n-octylamino, phenethylamino, iso-propoxypropylamino, ethoxypropylamino, n-hexyl ester group, n-heptyl ester group, n-octyl ester group, phenethyl ester group, iso-propoxypropyl ester group, and ethoxypropyl ester group.

2. The sesquiterpene derivative according to claim 1, wherein the sesquiterpene derivative has a structure represented by the structural formula I, wherein $R_1$ is the benzoate group or the p-hydroxybenzoate group.

3. A method for the treatment of hepatitis B diseases, comprising
administering a sesquiterpene derivative according to claim 1 to a subject in need of treatment thereof.

4. The method according to claim 3, wherein the hepatitis B diseases comprise hepatitis B virus-infected hepatitis, and liver damage diseases caused by hepatitis B virus infection.

5. The method according to claim 3, wherein the sesquiterpene derivative is combinable with a pharmaceutically acceptable carrier and/or an edible carrier.

6. The method according to claim 5, wherein the sesquiterpene derivative is contained in the medicament in a therapeutically effective dose.

7. The method according to claim 6, wherein the therapeutically effective dose is sufficient to downregulate hepatocyte nuclear factor 4α.

8. The method according to claim 5, wherein the medicament comprises oral administration preparations and non-oral administration preparations;
   the oral administration preparations comprise tablets, pills, capsules, granules, microencapsulated tablets, suspensions, dropping pills, and oral liquids; and
   the non-oral administration preparations comprise injections, aerosols, suppositories, and subcutaneous administration preparations.

\* \* \* \* \*